United States Patent
Signoff et al.

(10) Patent No.: US 8,588,913 B2
(45) Date of Patent: Nov. 19, 2013

(54) MULTIPLE BATTERY CONFIGURATIONS IN AN IMPLANTABLE MEDICAL DEVICE

(75) Inventors: David M. Signoff, San Clemente, CA (US); Marcus F. Julian, Dana Point, CA (US)

(73) Assignee: Cameron Health, Inc., San Clemente, CA (US)

( * ) Notice: Subject to any disclaimer, the term of this patent is extended or adjusted under 35 U.S.C. 154(b) by 109 days.

(21) Appl. No.: 13/102,944

(22) Filed: May 6, 2011

(65) Prior Publication Data
US 2011/0213434 A1 Sep. 1, 2011

Related U.S. Application Data

(63) Continuation of application No. 11/833,163, filed on Aug. 2, 2007, now Pat. No. 7,962,212.

(51) Int. Cl.
*A61N 1/08* (2006.01)

(52) U.S. Cl.
USPC .............................. 607/34; 320/121

(58) Field of Classification Search
USPC ............................................ 607/34; 320/121
See application file for complete search history.

(56) References Cited

U.S. PATENT DOCUMENTS

| | | | |
|---|---|---|---|
| 5,270,946 A * | 12/1993 | Shibasaki et al. | 713/340 |
| 5,369,351 A * | 11/1994 | Adams | 320/121 |
| 7,783,357 B2 * | 8/2010 | Brink et al. | 607/34 |
| 2006/0111752 A1* | 5/2006 | Greatbatch et al. | 607/34 |

* cited by examiner

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

Implantable medical device power circuits are disclosed. Multiple batteries may be provided, along with a number of switches, enabling a plurality of battery and power circuit configurations to be defined. Configurations of the power circuit may be changed in response to changes in battery status as the batteries are used and/or near end-of-life. Configurations of the power circuit may also be performed in response to changes in device operation. Methods associated with operating such circuits and implantable medical devices are also disclosed.

13 Claims, 13 Drawing Sheets

MULTIPLE BATTERY CONFIGURATIONS IN AN IMPLANTABLE MEDICAL DEVICE

RELATED APPLICATIONS

This application is a continuation of U.S. patent application Ser. No. 11/833,163, filed Aug. 2, 2007, published as U.S. 2009-0036943 A1, and titled MULTIPLE BATTERY CONFIGURATIONS IN AN IMPLANTABLE MEDICAL DEVICE, now U.S. Pat. No. 7,962,212, the entire disclosure of which is incorporated herein by reference.

FIELD

The present invention is related to the field of implantable medical devices. More particularly, the present invention relates to electric power supply systems in implantable medical devices.

BACKGROUND

Some implantable medical device operations require both low-power and high-power functions. An example is an implantable cardioverter-defibrillator (ICD). An ICD monitors cardiac function in a patient using implanted electrodes that capture electrical signals generated by the heart. This monitoring function requires the operation of low power control and analysis circuitry which may include, for example, amplifiers, filters, analog-to-digital converting hardware and/or or a microcontroller. The low power circuitry will use currents in the range of microamps at voltages that have been decreasing with improvements in digital and analog circuitry.

In an ICD, monitoring is performed in part to determine whether a malignant arrhythmia is occurring in a patient's heart. If a malignant arrhythmia is identified, high power circuitry is used to build up and then release a large amplitude stimulus to the patient. Such a stimulus may have a voltage of hundreds or even thousands of volts, with total power ranging from less than a Joule up to 80 or more Joules.

A challenge in designing an implantable medical device (IMD) is to find power supply circuitry which can meet the low and high power needs of the device. The simplest approach is to use a single battery. However, challenges arise because available batteries often come in one of two forms: batteries capable of delivering large currents (i.e., high power outputs) but lacking optimal energy density, and batteries having high energy density but which encounter large internal impedances at high currents. One approach could be to provide separate low and high power sources using separate batteries, one having high current output capacity and one having high energy density. However, using separate batteries would cause the device to be disabled as soon as one of the batteries reaches its end-of-life. Alternative solutions are desired.

SUMMARY

The present invention, in an illustrative embodiment, includes an implantable medical device comprising at least first and second batteries and switching circuitry associated with the first and second batteries. In an illustrative example, a plurality of configurations are provided by the switching circuitry such that, in a first configuration, the batteries operate in parallel with anodes and cathodes coupled together, equalizing voltage output; in a second configuration, the batteries operate in series with the anode of one battery coupled to the cathode of the other battery such that low and high power outputs may be taken from the nodes at each of the anodes; in a third configuration, the batteries are isolated from one another. More than two batteries may be used. Some embodiments include configurations in which one or more batteries may be entirely excluded from operation, if so desired, for example, after it is determined that a battery is near its effective end-of-life. Additional illustrative embodiments include methods associated with such devices. In another embodiment, the configuration of a power circuit in an implantable medical device is selected in response to changes in device state or operation.

DETAILED DESCRIPTION

The following detailed description should be read with reference to the drawings. The drawings, which are not necessarily to scale, depict illustrative embodiments and are not intended to limit the scope of the invention.

Figure 1A:
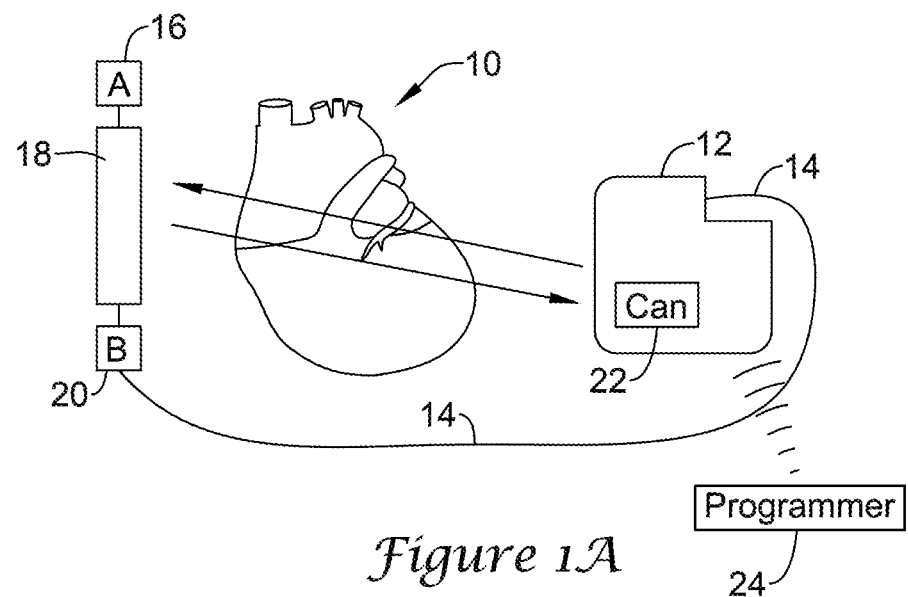
FIGS. 1A-1B show respective subcutaneous and transvenous implantable cardiac stimulus systems.
Figure 1B:
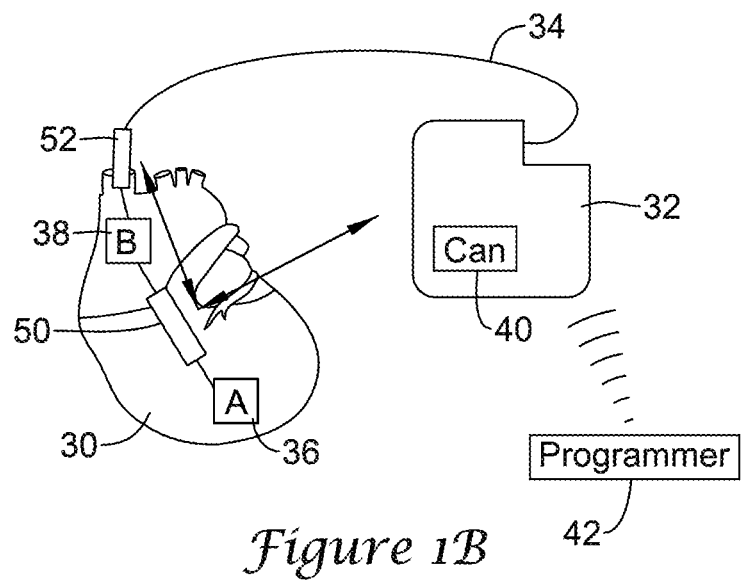

FIGS. 1A-1B, respectively, show subcutaneous and transvenous implanted cardiac stimulus systems relative to a patient's heart. Referring to FIG. 1A, the heart 10 is shown in relation to an implanted, subcutaneous cardiac stimulus system including a canister 12. A lead 14 is secured to canister 12 and includes sensing electrode A 16, a coil electrode 18, and sensing electrode B 20. A can electrode 22 is shown on the canister 12. Other electrode configurations may be used. An alternative subcutaneous system uses a flexible unitary housing rather than a can 12, with or without a lead. Illustrative subcutaneous systems are shown in U.S. Pat. Nos. 6,647,292 and 6,721,597, and the disclosures of these patents are incorporated herein by reference.

A vector for delivering cardiac stimulus is defined between the can electrode 22 and the coil electrode 18. Other vectors for stimulus delivery may be defined depending upon the internal circuitry of the device, different lead designs, and/or the size and shape of electrodes A and B 16, 20, which may also be used for stimulus delivery if so suited. The stimulus vector is illustrated as having two polarities. In addition, although not shown, a number of sensing vectors are defined, for example, using combinations of electrode A 16, electrode B 20, can electrode 22, and/or, if desired, coil electrode 18.

Referring now to FIG. 1B, a transvenous system is shown relative to a patient's heart 30. The transvenous cardiac stimulus system includes a canister 32 connected to a lead 34. The lead 34 resides partly within the patient's vasculature, enters the patient's heart, and includes sensing electrodes A 36 and B 38. Stimulus electrodes are shown at 50, 52. The lead 34 may be anchored into the patient's myocardium. Again, a can electrode 40 is shown on the canister 32. With this system, plural sensing and stimulus delivery vectors may be defined. The embodiment shown includes two stimulus delivery vectors each having two polarities, that is, stimulus vectors between electrodes 50 and 52 and between electrodes 40 and 50. A third stimulus vector may also be defined between electrodes 40 and 52, although this is not shown in the illustration. Other lead and electrode configurations may also be used.

Each of the devices 12, 32 may further include such components as would be appropriate for communication (such as RF communication, inductive telemetry or other suitable communication linkage) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate the implanted device 12, 32, and/or direct/observe diagnostic or operational tests. After implantation, the programmer 24, 42 may be used to non-invasively determine the status and history of the implanted device. The programmers 24, 42 in combination with the implanted devices 12, 32 may also allow annunciation of statistics, errors, history and potential problems to the user/medical practitioner, and may also allow for updating of programming in the implanted devices 12, 32.

The systems shown in FIGS. 1A-1B are merely illustrative. The present invention may be embodied in virtually any implantable system. For example, it may be embodied in transvenous or subcutaneous systems such as those shown in FIGS. 1A-1B, as well as hybrid systems combining features of both. Additionally, the present invention may also be embodied in fully intravascular systems modeled on those shown in US Patent Application Publication Number 2006-0224225 A1, now U.S. Pat. No. 7,734,343, (Ransbury et al.). Although explained in the context of a cardiac stimulus system, the present invention may also be embodied in other implantable medical systems directed toward other portions of the anatomy.

Figure 2:
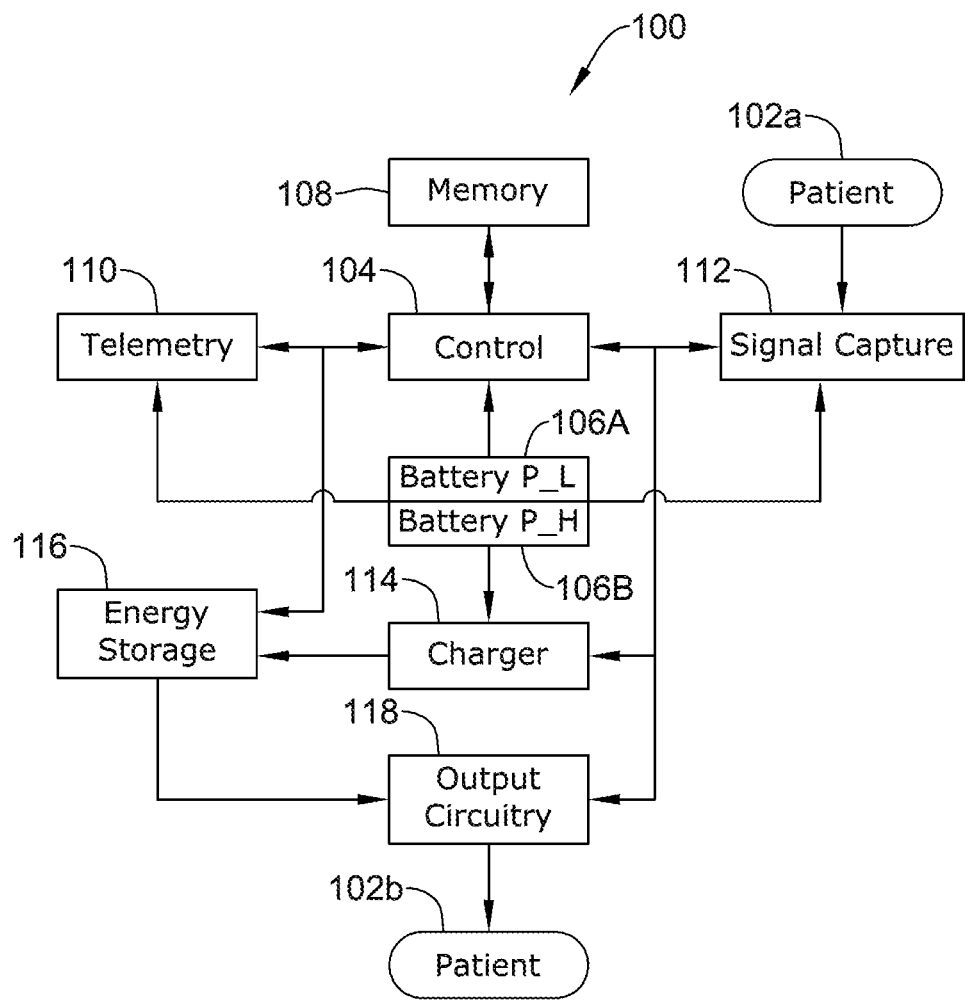
FIG. 2 is a functional block diagram for an illustrative implantable medical device.

FIG. 2 is a functional block diagram for an illustrative implantable cardiac stimulus device. In the illustrative example, operational circuitry for an implantable cardiac stimulus device is shown at 100, a patient is shown both at 102a and 102b. It should be understood that this is the same patient in both instances 102a, 102b, but the coupling electrodes may be different for each. For example, shock delivery electrodes may be separate or different from sensing electrodes, although this need not always be the case.

The operational circuitry includes a control block 104, which may take any suitable or conventional form. Microcontrollers are one class of device that may be used in control block 104, although in addition to or as a replacement for a microcontroller, there may be various logic and other devices or subcircuits. The control block 104 may access a memory 108, which may take various forms including RAM, ROM, Flash memory, or any other suitable form (optical, electrical, magnetic, etc.) for temporarily or permanently storing information and/or instruction sets. The control block 104 is configured and connected to other circuitry within the device such that it can direct operations associated with methods of practicing some illustrative embodiments of the present invention. A battery block 106 is also shown. The battery block 106 is more fully explained below.

The operational circuitry 100 may also include telemetry 110, which may include such drivers, mixers, antenna(s), amplifiers and the like as are known for use in communications circuitry. The telemetry 110 is used to communicate with a programmer, such as programmers 24, 42 shown in FIGS. 1A-1B.

Signal capture block 112 includes amplifying and filtering circuitry which may take any form suitable for use in an implantable cardiac stimulus device for observing cardiac function. Signal capture block 112 may also including sampling and analog-to-digital devices, as well as local registers, memory or the like for temporarily storing captured information.

Generally speaking, the control block 104 uses the signal capture block 112 to capture data from the patient 102a. In response to instructions from telemetry 110 and/or instructions or data stored in memory 108, the control block 104 may analyze data from the signal capture block 112 to determine whether the patient 102a/b is in need of stimulus. If so, the control block 104 calls on the charger 114 to charge energy storage 116, which may include one or more capacitors in any suitable configuration. As is known to those of skill in the art, the charger 114 is used to step up the voltage from the battery 106 (typically less than 10 volts) to a higher level (up to several hundred or even several thousand volts) for use in cardioversion or defibrillation. In order to achieve sufficient energy storage, the charger 114 typically draws significantly larger currents than other portions of the operational circuitry 100.

The control block 104 and/or the charger 114 may monitor the voltage level on the energy storage 116 during charging to determine whether and when sufficient stimulus energy has been stored. Once enough energy is stored at energy storage 116 for stimulus delivery, the control block 104 manipulates output circuitry 118, which may include, for example, a plurality of switches and/or an H-bridge configuration, in order to deliver the stored energy to the patient 102b. An H-bridge is shown, for example, in U.S. Pat. Nos. 6,865,417 and 6,952,608. In other medical devices, there may be output circuitry, such as transducers (such as sonic drivers for phoresis delivery of a drug), pumps, etc., that take the place of the illustrative subcircuits shown at 114, 116 and 118 in FIG. 2.

In the illustration, the battery block 106 is shown as providing a Low Power portion 106A, which powers the control block 104, telemetry 110, and signal capture block 112. For illustrative purposes, not all connections are shown. The battery block 106 also includes a High Power portion 106B, which is used to power a charger 114.

In an illustrative example, the control block 104 can manipulate the duration and format of the applied stimulus by controlling the output circuitry 118, for example, controlling whether the applied waveform is monophasic or biphasic, and also controlling the amplitude and polarity. It is typical for the amplitude of the applied voltage to drop during its application as the energy storage 116 (typically a bank of capacitors) discharges energy. The change in output amplitude during an applied pulse is sometimes referred to as "tilt," a ratio of the final voltage to the initial voltage. Constant current stimuli may also be applied.

Figure 3:
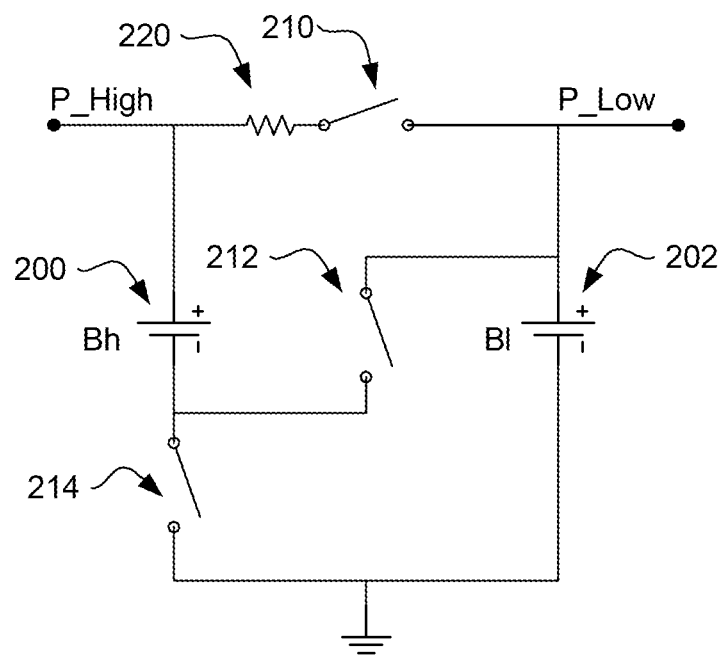
FIG. 3 is a schematic for an illustrative embodiment.

FIG. 3 is a schematic for an illustrative embodiment of a power system. The illustrative embodiment includes a high output battery Bh, shown at 200, and a low output battery Bl, shown at 202. The batteries 200, 202 are coupled to high and low outputs shown, respectively, at P_High and P_Low, which are taken with respect to a common ground, as shown. Three switches 210, 212, and 214 selectively couple the batteries 200, 202 to the outputs, ground, and each other. An optional attenuating resistor is shown at 220.

The switches 210, 212, 214 may take any suitable form, including for example, MOSFET, JFET and/or BJT electrical devices. Other devices, such as relays and/or silicon controlled rectifiers, may also be used. It should be understood that control wires for these switches 210, 212, 214 have been omitted from the Figures for simplicity.

As shown, switch 212 selectively couples the positive terminal + of the low output battery Bl 202 to the negative terminal − of the high output battery Bh 200. Switch 214 selectively couples the negative terminal of the high output battery Bh 200 to ground. The positive terminal of the high output battery Bh 200 is directly coupled to a P_High output of the battery subcircuit, while the positive terminal of the low output battery Bl 202 is directly coupled to a P_Low output of the battery subcircuit. The operation of the switches to provide multiple configurations is further illustrated below by reference to FIGS. 4A-4C.

In an illustrative example, P_High is used to power high current portions of the implantable device circuitry, and P_Low is used to power low current portions of the implantable device circuitry. For example, in an ICD, P_High is used to power charging circuitry that quickly stores up energy on power capacitors for delivering as a defibrillation pulse, while P_Low can power the control circuitry. In another illustrative example, P_High is element 106B in FIG. 2, while P_Low is element 106A in FIG. 2.

In an illustrative example, the batteries 200 and 202 may differ in chemistry and/or structure such that each has distinct characteristics. For example, the low output battery 202 may be a battery having relatively higher internal impedance than the high output battery 200, but higher energy density, making the low output battery 202 well suited to providing power for long-term operation of control and monitoring circuitry, while the high output battery 200, with the lower internal impedance, would be better suited to powering high current applications such as charging a high power capacitor for use in delivering large stimulus. In an alternative embodiment, the batteries 200, 202 may be of the same construction as one another.

Figure 4A:
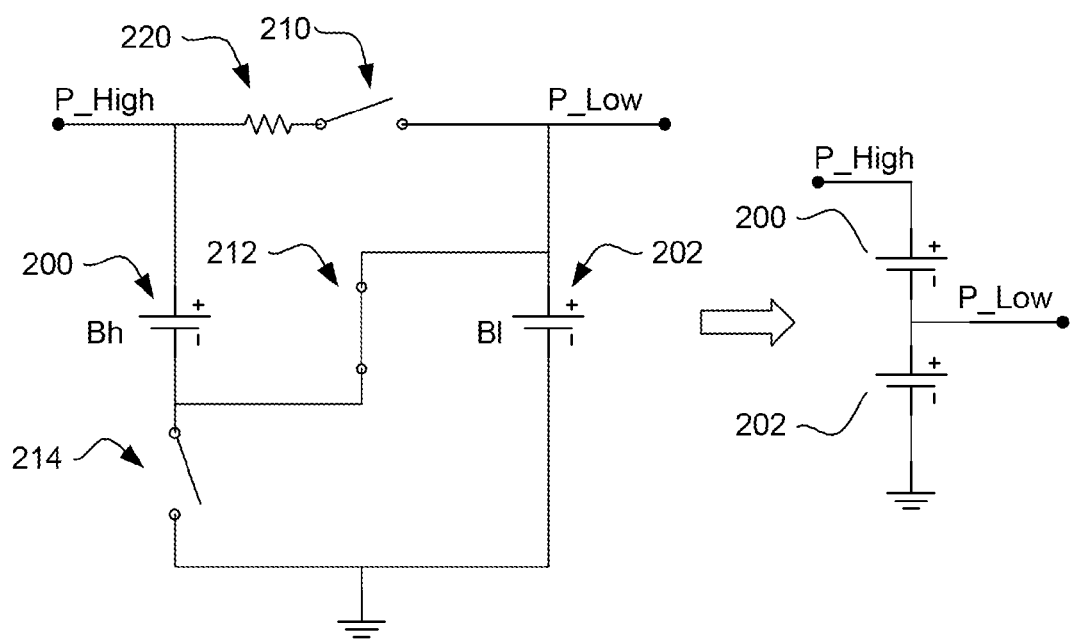
FIGS. 4A-4C show the illustrative embodiment of FIG. 3 in three configurations.
Figure 4B:
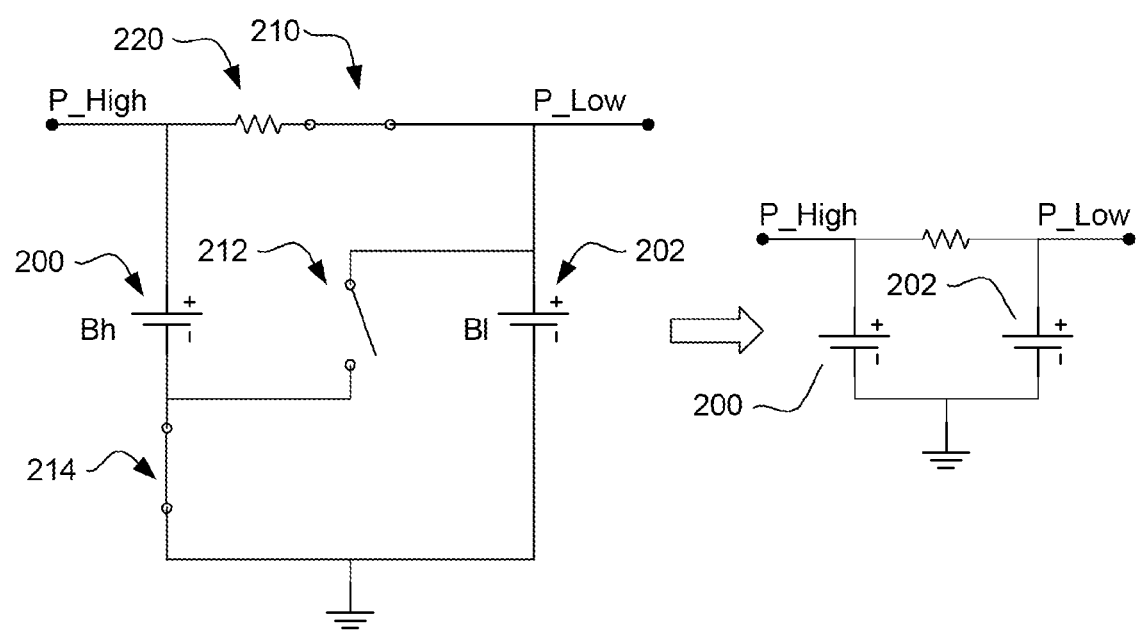
Figure 4C:
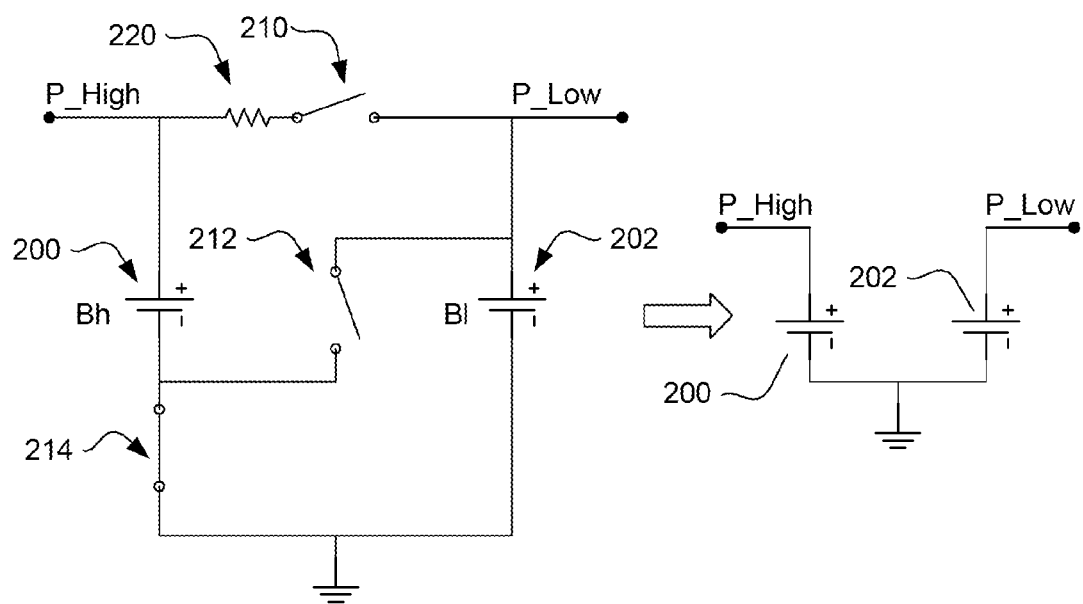

FIGS. 4A-4C show the illustrative embodiment of FIG. 3 in three configurations. In FIG. 4A, switch 212 is closed, while switches 210 and 214 are open. This couples the positive terminal + of the low output battery 202 to the negative terminal − of the high output battery 200, placing the batteries 200, 202 in series. The output of the series is at P_High, and an output is taken between the batteries 200, 202, as P_Low. The illustration to the right of the drawing shows this simplified circuit. The voltage at P_High will be the sum of the voltages across the batteries 200, 202, which in turn reduces the equivalent current draw at P_High during high power output, since less current is drawn to produce the same power output at this summed voltage.

In FIG. 4B, switch 212 is left open, while switches 214 and 210 are closed. As shown to the right, this configuration places P_High and P_Low in parallel connection with one another across the optional resistor 220, which may be omitted if desired. This configuration allows either battery 200, 202 to make up for a deficiency of the other battery. The optional resistor 220 can be used to prevent shorting of one battery 200/202 to the other 202/200, for example, if the batteries 200, 202 have different output voltages. Alternatively, the optional resistor 220 may be omitted to prevent attenuation of energy within the circuit.

In an alternative configuration, an additional switch may be placed between the negative terminal of the low output battery 202 and ground. This switch may be opened to remove the low output battery 202 from the circuit entirely, which may be desired if the low output battery 202 reaches or nears its end-of-life. Then all circuitry would be powered from the other battery. Conversely, the configuration of FIG. 4B may be modified to open switch 214, removing the high output battery 200 from the circuit entirely, since the negative terminal of the high output battery 200 would then be left floating. This would allow the low output battery 202 to power the entire device in the event that the high output battery 200 reaches or nears its end-of-life. In some embodiments, each battery may be individually tested to determine whether either is at or near its end-of-life, for example, by monitoring changes in internal impedance, loaded voltage, or open circuit voltage.

In some illustrative examples, battery status may be measured by one or more of the following methods. An illustrative method may include coupling a battery output to a high impedance input to an analog-to-digital converter to check open circuit voltage. Another illustrative method may include measuring a voltage across a resistor, to check loaded voltage of the battery. If both such measurements are taken, yielding Vopen and Vloaded, and the resistor size is known, the internal impedance of a battery may be identified by noting that the resistor and the internal resistance of the battery form a voltage divider, with:

$$V_{Open} = V_{Loaded} \times \frac{R_{Load} + R_{Internal}}{R_{Load}}$$

Solving for the internal resistance:

$$R_{Internal} = R_{Load} \times \left(\frac{V_{Open}}{V_{Loaded}} - 1\right)$$

Another method of measuring battery status is disclosed in U.S. patent application Ser. No. 11/487,103, titled END OF LIFE BATTERY TESTING IN AN IMPLANTABLE MEDICAL DEVICE, filed on Jul. 14, 2006, and published as US 2008-0015644 A1, the disclosure of which is incorporated herein by reference. Any of these methods and metrics (open circuit voltage, loaded voltage, and internal impedance or resistance) may be used to determine battery status and estimate the end-of-life (EOL) for a battery. Additional methods, devices and sub-circuits for testing any of these metrics, or other metrics indicating battery status, are known in the art as well. Battery status may be annunciated to an associated programmer when queried or whenever a battery nears EOL. If EOL approaches or occur, the device may notify an implantee, as is known in the art.

In yet another embodiment, a switch is supplied between the positive terminal of the low output battery 202 and the P_Low output, with the configuration of FIG. 4A being used. In this manner, the two batteries 200, 202 can be used in series to supply power for both the P_High and P_Low outputs; this may be desired when either or both batteries are near end of life. While it is likely best that a patient seek medical attention, likely including explant and replacement of the device, when end of life for either or both batteries is near, the device itself, as implanted, can be configured to maximize the available battery power even if the patient delays in obtaining medical attention.

FIG. 4C demonstrates yet another configuration. Here, switches 210 and 212 are left open, isolating the batteries from one another. The result is that the P_High output is provided exclusively by the high output battery 200, and the P_Low output is provided exclusively by the low output battery 202.

Usage of these configurations may be programmed into a device. The configuration of FIG. 4C may be used, in this example, as a default or standard configuration during ordinary operation of an implantable medical device (IMD) such as an ICD. If the ICD is also equipped to provide a pacing output, the configuration of FIG. 4C may be used during pacing, with P_High and hence only the high output battery 200 used to provide pacing output energy, while P_Low and hence only the low output battery 202 used to power associated control circuitry. If a defibrillation or cardioversion stimulus is used, either the configuration of FIG. 4C or the configuration of FIG. 4A may be used. In one example, the power supply switches are adjusted to the configuration of FIG. 4A in the event that a high voltage pulse charge fails to build on associated capacitors within a predetermined period of time. In another example, the configuration of FIG. 4A is used when multiple large amplitude stimuli are needed within a short period of time. In yet another example, an ICD is configured to provide defibrillation pulses having increasing amplitudes (i.e., 5 Joules, 10 Joules, 15 Joules, etc.), and the configuration of FIG. 4C is used for lesser amplitudes, while the configuration of FIG. 4A is used for greater amplitudes. The configuration of FIG. 4B may be used near the end of life of the low output battery 202.

Figure 5:
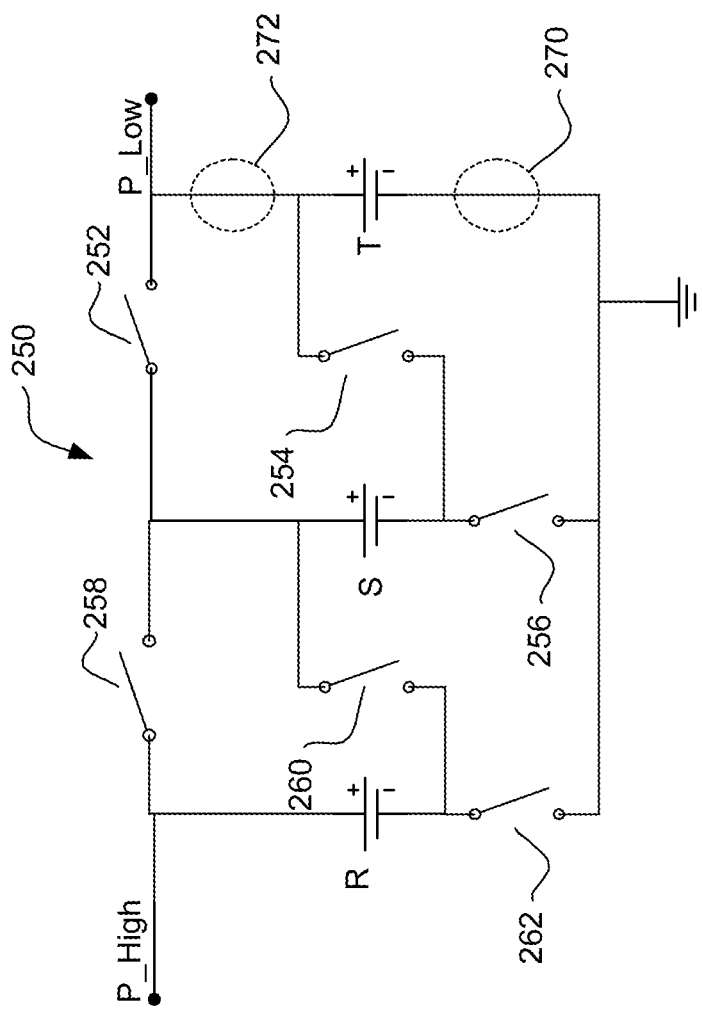
FIG. 5 is an illustrative embodiment having three batteries.

FIG. 5 is an illustrative embodiment of a power system 250 having three batteries. In the illustrative embodiment, batteries R, S, and T are shown coupled together with a plurality of switches 252, 254, 256, 258, 260, 262. It can be seen, when compared to FIG. 3, that the embodiment of FIG. 5 is similar except that a module of battery R and switches 258, 260, 262 has been added.

The following chart is illustrative of operation:

| Configuration | 252 | 254 | 256 | 258 | 260 | 262 | P_High | P_Low |
|---|---|---|---|---|---|---|---|---|
| 1 | O | X | O | O | X | O | R + S + T | T |
| 2 | X | O | X | X | O | X | R = S = T | R = S = T |
| 3 | X | O | O | X | O | X | R + T | T |
| 4 | O | X | O | X | O | O | S + T | T |
| 5 | O | O | X | O | X | O | R + S | T |

Additional configurations can be added as well. Configuration 1 allows all three batteries to contribute during a high power output time period. Configuration 2 allows each battery to contribute to high and low power output, for example, to compensate for one of the batteries being at or near its end-of-life. Configuration 3 allows a battery, in this case, battery S, to be isolated, while configuration 4 allows a different battery, in this case, battery R, to be isolated. Configuration 5 separates the functions of the batteries completely such that two batteries are dedicated to only high power output P_High while the third battery is dedicated to only the low power output P_Low.

Those of skill in the art will recognize that the pattern and configuration in FIG. 5 can be expanded using 3(N−1) switches to couple N batteries together. Those of skill in the art will also recognize that an additional switch may be provided at one of locations 270, 272 to allow isolation of battery T in a manner analogous to configurations 3 and 4 shown above. An example includes another switch at location 272: switches 256 and 260 would be closed such that P_High=S+R, and switch 252 is closed such that P_Low=S, while switches 254, 258, 262 and 272 are opened, with switches 254 and 272 isolating battery T, and switches 258 and 262 being opened to allow series operation of batteries S and R for output P_High.

Figure 6:
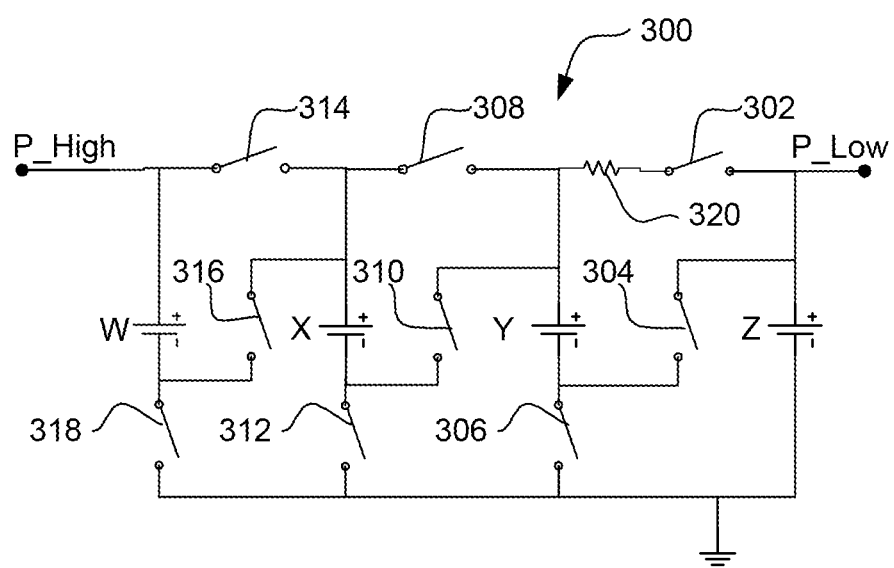
FIG. 6 is an illustrative embodiment having four batteries.

FIG. 6 is an illustrative embodiment of a power system having four batteries. The embodiment in FIG. 6 includes yet another "module" comprising battery W and switches 314, 316, 318, as compared to FIG. 5. Batteries W, X, Y and Z are shown and coupled together. Switches 304, 310 and 316 selectively couple battery pairs in series with positive terminals coupled to negative terminals for battery pairs Z/Y, Y/X, and X/W, respectively. Switches 306, 312, 318 selectively couple the negative terminals of batteries Y, X and W, respectively, to ground. Switches 302, 308 and 314 selectively couple positive terminals of pairs of batteries together, with switch 302 between batteries Z/Y, switch 308 between batteries Y/X, and switch 314 between batteries X/W. Again, an optional resistor is shown at 320. The interconnections of the batteries W, X, Y, Z and switches 302, 304, 306, 308, 310, 312, 314, 316 and 318 form a power system.

Figure 7A:
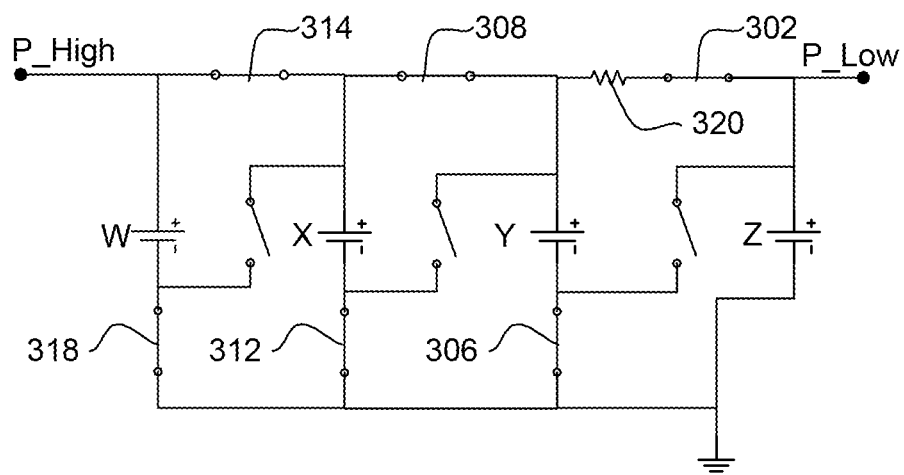
FIGS. 7A-7C show the illustrative embodiment of FIG. 6 in three configurations.
Figure 7B:
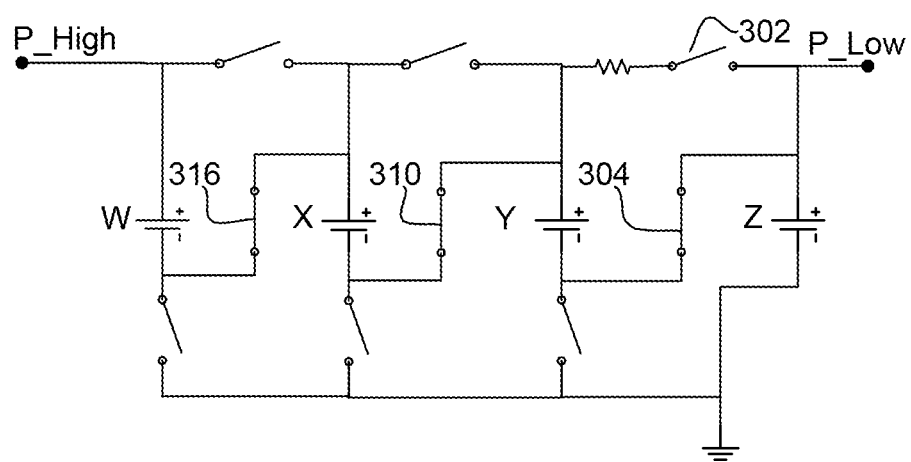
Figure 7C:
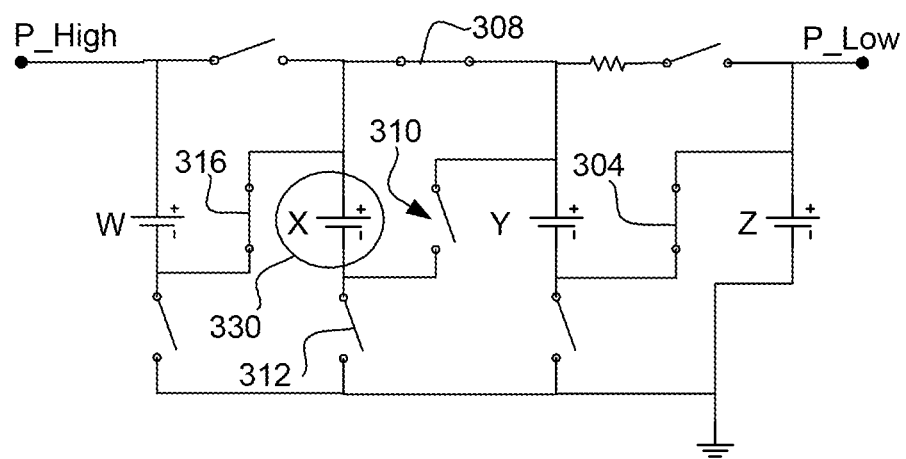

FIGS. 7A-7C show the illustrative embodiment of FIG. 6 in three configurations. In FIG. 7A, all of the batteries are connected in parallel with one another by having switches 302, 306, 308, 312, 314 and 318 closed. In FIG. 7B, P_Low is taken from battery Z only by opening switch 302, and the P_High is taken from the series combination of batteries W, X, Y, and Z by closing switches 304, 310 and 316, while leaving other switches open, as shown. FIG. 7C shows a configuration in which one battery (battery X) is excluded from the circuit as indicated at 330, which may be necessary if one of the batteries becomes depleted faster than other batteries; alternatively, this may simply be a configuration deliberately chosen for other design purposes. Battery X is excluded by closing switches 304, 308 and 316 and opening switches 310, 312, thereby routing current around the excluded battery X.

Figure 7D:
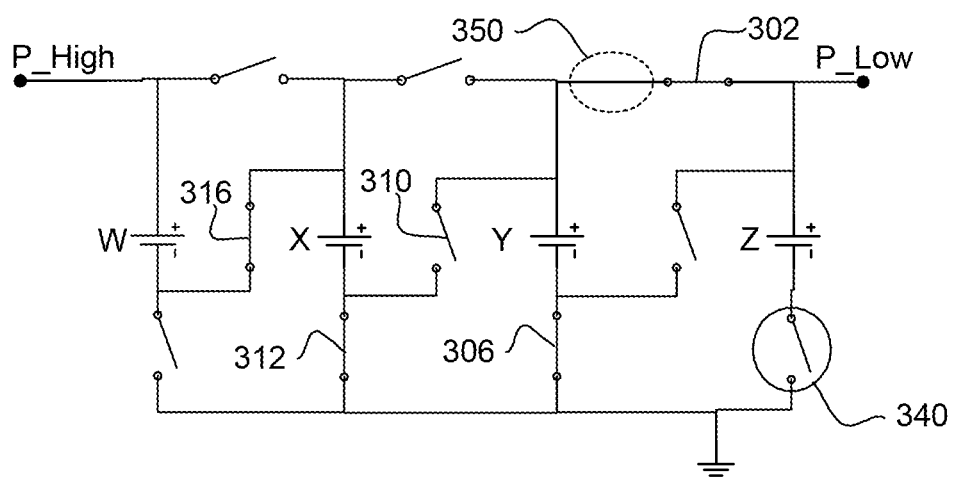
FIG. 7D shows an alternative construction and configuration for the embodiment of FIG. 6.

FIG. 7D shows an alternative construction and configuration for the embodiment of FIG. 6. This construction includes an additional switch 340 in series with battery Z and located between the negative terminal of battery Z and ground, and the otherwise optional resistor is omitted as indicated at 350. In this configuration, opening switch 340 allows battery Z to be excluded from the circuit. In the configuration shown, P_Low is powered by battery Y alone, while P_High is powered by batteries W and X in series with one another by closing switches 312 and 316, while the other switches remain open. The additional switch may be included in other configurations shown herein such that the number of switches in each would then be 3N−2 for N batteries.

In an illustrative example, battery Z may be a battery used by default to power P_Low (for example, battery Z may be of different chemistry or construction than batteries W, X and Y). In this example, battery Z may near or reach end-of-life well before the other batteries if the device is implanted for prophylactic purposes in a patient who rarely needs high power therapy, as may happen if a high risk patient eliminates risk factors by changes to habits, diet, exercise and/or medication and sees substantial improvement. In this scenario, the remaining batteries may be reconfigured as shown to provide a low power output P_Low without continued reliance on the end-of-life battery. As an alternative to that shown in FIG. 7D, switch 310 may be closed while switch 312 is opened, allowing the P_High output to be generated by the series combination of all three of batteries W, X and Y.

In an illustrative example, at least one of the batteries is coupled to the P_Low node in series with a switching device that is "closed" when no voltage is applied. For example, switch 340 may be a depletion-type MOSFET, which turns off when a voltage is applied to its control terminal. This may simplify device turn-on, since at least one battery is coupled between P_Low and ground without any voltage output from a control terminal to the depletion-type MOSFET.

Figure 8:
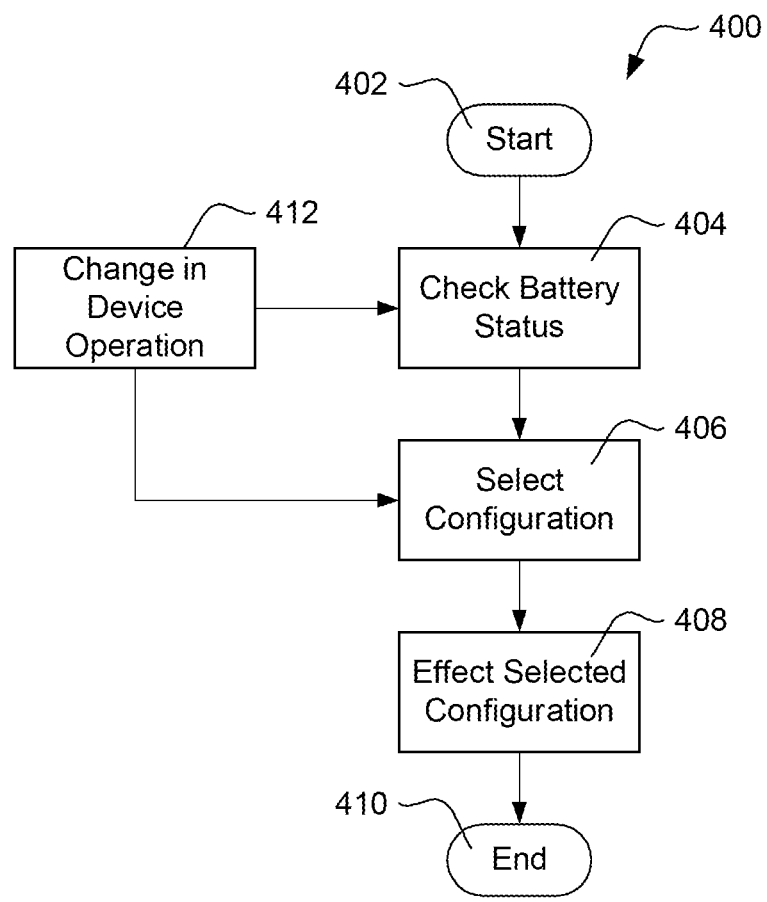
FIG. 8 is a process flow diagram showing an illustrative method.

FIG. 8 is a process flow diagram showing an illustrative method. The method 400 may begin from a start block 402, which will in some embodiments be initiated at intervals, for example, daily, weekly or at lesser or greater intervals. The method 400 may also be initiated in response to a query during a session in which communication is established between an implanted device and a programmer.

First, battery status is checked, as indicated at 404. In some embodiments, all batteries in the system may be checked during step 404. Alternatively, only batteries which are known to have produced currents during operation may be tested, for example, in an ICD, it is possible for monitoring of cardiac activity, which is a relatively low power function of the device, to occur for a great period of time without any stimuli being delivered to an implant recipient. In this instance, the method may perform a battery status check on only the battery(ies) that are powering the low power functions. In yet another embodiment, all batteries are checked to monitor for conditions that indicate device or battery malfunction. Although not shown, in response to step 404, a flag or other stored value may be set by the implanted device to indicate the battery status and/or if one or more batteries are at or near end-of-life. If and when communication is established with an external programmer, such flags or values may be annunciated.

From step 404, the device continues to step 406, in which a battery configuration is selected. Next, the selected battery configuration is effected, a shown at 408, by opening and/or closing appropriate switches in the power supply circuit. The method then ends, as shown at 410. In an illustrative example, an indicator of the configuration in use can be stored and this indicator is annunciated during communication with an external programmer.

In addition to periodic starting at 402, in some embodiments, a change in device operation 412 may cause initiation of method 400. This may occur, for example, when it is determined that a high power output is needed from the power supply circuit, for example, when a malignant arrhythmia is detected by an ICD and stimulus is needed, or when a bradyarrhythmia is detected by a pacemaker and pacing is indicated, or when stimulus of another portion of patient anatomy, such as parts of the nervous system, is needed. In one example of an ICD, the change in device operation may also occur during operation if multiple stimuli are delivered at increasing amplitudes. The change in device operation 412 may occur if a time-out occurs during charging of a high power capacitor in an ICD as may happen if the previously selected configuration fails to provide adequate current/power to charge the high power capacitor quickly. In another example, the implanted medical device may be a drug delivery device having output circuitry for delivering a drug to a patient, or having a pump that requires operation, and the decision to deliver the drug represents a change in device operation. Similarly, block 412 may be an indication that use of the high power output has ended, such that a different configuration adapted for delivery of only low power output may be adopted.

Initiation of method 402 from block 412 may go to either block 404 or block 406. For example, if the method is embodied in an ICD and a high power stimulus is to be delivered to prevent sudden cardiac death, a new configuration 406 may be selected without re-checking battery status, in order to reduce delay between the decision to deliver stimulus and actual stimulus delivery. Alternatively, in a device such as an insulin pump, a delay of a few seconds to allow battery status to be checked in step 404 may be acceptable.

In the example of an ICD, if the change in device operation occurs due to a time-out occurring during high power capacitor charging, a check of battery status 404 may be performed to determine why the time-out occurred—and, if one or more batteries is at or near end-of-life, to remove the offending battery from the high power output circuit. For example, a battery at or near its end-of-life may undergo an increase in internal impedance, which may introduce a time constant into the charging circuitry that prevents fast charging. If such a battery is placed in series with the high power output, one "dead" battery in series with one or more non-depleted batteries can prevent the other batteries from successful charging.

In an illustrative embodiment, the select configuration step 406 may include determining whether a change in battery configuration is appropriate. For example, the previous/current battery configuration may be checked in light of a change in device operation, and if the configuration is appropriate for the change of device operation which has or is occurring, then the previous/current battery configuration may be left in place. Otherwise, a different configuration is selected.

Those skilled in the art will understand that reference to "ground" or a "ground node" indicates a reference node for the system and does not imply or require an actual connection to an earth ground or other external environment reference.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of operating an implantable device comprising power circuitry including at least first, second and third batteries, the implantable device further comprising control circuitry for controlling device operation and sensing circuitry for sensing a biological state of a patient in whom the implantable device is placed, the method comprising:
 at a first time, providing power for the control circuitry and sensing circuitry of the implantable device using each of the first, second and third batteries, wherein the implantable device comprises a plurality of switches enabling one or more of the first, second and third batteries to be isolated from the other batteries such that, at the first time, the switches are configured to allow each of the first, second and third batteries to provide power to the control and sensing circuitry;
 testing the first, second and third batteries to identify whether one or more of the first, second and third batteries is at or approaching end-of-life (EOL);
 identifying one of the first, second and third batteries as being at or approaching EOL; and
 at a second time after the identification of a battery that is at or approaching EOL:
  manipulating the switches to isolate the battery that is at or approaching EOL; and
  providing power for the control circuitry and sensing circuitry of the implantable device using the remaining batteries excluding the battery that is at or approaching EOL;
 wherein the implantable device is an implantable defibrillator comprising high power circuitry including a delivery capacitor for delivering defibrillation therapy and converter circuitry for receiving power from the power circuitry and charging the delivery capacitor.

2. The method of claim 1 wherein the method further comprises, if a battery that is at or approaching EOL is identified, generating a warning to a recipient of the implantable device.

3. The method of claim 1 wherein the step of testing the first, second and third batteries to identify whether one or more of the first, second and third batteries is at or approaching EOL includes one or more methods selected from the group consisting of:
testing an open circuit voltage of a battery,
testing a loaded voltage of a battery, and
calculating an effective series resistance of a battery.

4. The method of claim 1 wherein the power circuitry further comprises a fourth battery.

5. The method of claim 1 wherein the biological state comprises a cardiac rhythm.

6. A method of operating an implantable device comprising power circuitry including at least first, second and third batteries, the implantable device further comprising control circuitry for controlling device operation and sensing circuitry for sensing a biological state of a patient in whom the implantable device is placed, the method comprising:
at a first time, providing power for the control circuitry and sensing circuitry of the implantable device using each of the first, second and third batteries, wherein the implantable device comprises a plurality of switches enabling one or more of the first, second and third batteries to be isolated from the other batteries such that, at the first time, the switches are configured to allow each of the first, second and third batteries to provide power to the control and sensing circuitry;
testing the first, second and third batteries to identify whether one or more of the first, second and third batteries is at or approaching end-of-life (EOL);
identifying one of the first, second and third batteries as being at or approaching EOL; and
at a second time after the identification of a battery that is at or approaching EOL:
manipulating the switches to isolate the battery that is at or approaching EOL; and
providing power for the control circuitry and sensing circuitry of the implantable device using the remaining batteries excluding the battery that is at or approaching EOL;
wherein the power circuitry for the implantable device drives a charger included in a high power circuit configured to deliver therapy, the charger being used to charge a capacitor for therapy delivery, wherein the high power circuit is fed, at the first time, by each of the first, second and third batteries in series, and at the second time, by at least two of the first, second and third batteries in series but excluding the battery that is at or approaching EOL.

7. The method of claim 6 wherein the power circuitry for the implantable device drives a low power circuit wherein the low power circuit is fed, at the first time, by one or more of the first, second or third batteries alone or in parallel, and at the second time, by one or more of the first, second or third batteries alone or in parallel but excluding the battery that is at or approaching EOL.

8. An implantable device comprising:
power circuitry including at least first, second and third batteries and a plurality of switches enabling one or more of the first second and third batteries to be isolated from the other batteries; and
operational circuitry for controlling operation of the power circuitry,
wherein the operational circuitry is configured to operate the power circuitry using a method comprising:
at a first time, providing power for the implantable device using each of the first, second and third batteries, including providing power to the operational circuitry;
testing the first, second and third batteries to identify whether one or more of the first, second and third batteries is at or approaching end-of-life (EOL);
identifying one of the first, second and third batteries as being at or approaching EOL; and
at a second time after the identification of a battery that is at or approaching EOL:
manipulating the switches to isolate the battery that is at or approaching EOL; and
providing power for the implantable device, including the operational circuitry,
using the remaining batteries excluding the battery that is at or approaching EOL;
wherein the implantable device is an implantable defibrillator comprising high power circuitry including a delivery capacitor for delivering defibrillation therapy and converter circuitry for receiving power from the power circuitry and charging the delivery capacitor.

9. The implantable device of claim 8 wherein the operational circuitry is configured to generate a warning to a recipient of the implantable device if a battery that is at or approaching EOL is identified.

10. The implantable device of claim 8 wherein the operational circuitry and power circuitry are configured such that testing the first, second and third batteries to identify whether one or more of the first, second and third batteries is at or approaching EOL includes one or more methods selected from the group consisting of:
testing an open circuit voltage of a battery,
testing a loaded voltage of a battery, and
calculating an effective series resistance of a battery.

11. The implantable device of claim 8 wherein the power circuitry further comprises a fourth battery.

12. An implantable device comprising:
power circuitry including at least first, second and third batteries and a plurality of switches enabling one or more of the first second and third batteries to be isolated from the other batteries; and
operational circuitry for controlling operation of the power circuitry,
wherein the operational circuitry is configured to operate the power circuitry using a method comprising:
at a first time, providing power for the implantable device using each of the first, second and third batteries, including providing power to the operational circuitry;
testing the first, second and third batteries to identify whether one or more of the first, second and third batteries is at or approaching end-of-life (EOL);
identifying one of the first, second and third batteries as being at or approaching EOL; and
at a second time after the identification of a battery that is at or approaching EOL:
manipulating the switches to isolate the battery that is at or approaching EOL; and
providing power for the implantable device, including the operational circuitry, using the remaining batteries excluding the battery that is at or approaching EOL;

wherein the operational circuitry is configured such that the method includes the power circuitry driving a charger included in a high power circuit configured to deliver therapy, the charger being used to charge a capacitor for therapy delivery, at the first time, by each of the first, second and third batteries in series, and at the second time, by at least two of the first, second and third batteries in series but excluding the battery that is at or approaching EOL.

13. The implantable device of claim 12 wherein the operational circuitry is configured such that the method includes the power circuitry driving a low power circuit wherein the low power circuit is fed, at the first time, by one or more of the first, second or third batteries alone or in parallel, and at the second time, by one or more of the first, second and/or third batteries alone or in parallel but excluding the battery that is at or approaching EOL.

* * * * *